ORANGE TREE

Filed March 28, 1950 2 SHEETS—SHEET 1

Bertman V. Johnson
INVENTOR.

BY Clarence A. O'Brien and Harvey B. Jacobson
Attorneys

Bertman V. Johnson
INVENTOR.

BY Clarence A. O'Brien and Harvey B. Jacobson
Attorneys

Patented Feb. 24, 1953

Plant Pat. 1,170

UNITED STATES PATENT OFFICE 1,170

ORANGE TREE

Bertman V. Johnson, Altoona, Fla.

Application March 28, 1950, Serial No. 152,365

1 Claim. (Cl. 47—62)

My new variety of orange tree is an improvement over the well-known commercial variety, the Parson Brown (unpatented). Several years ago, the bud on a Parson Brown orange tree located on my property in Marion County, Florida, was shield budded to a small sour seedling orange tree that produced a bud sprout which grew into a tree. When this tree matured wood for suitable budding stock, part of it was cut off to bud other sour seedling orange trees, and at present there are a number of trees bearing noticeable amounts of fruit, all the trees remaining true to type.

Figure 1:
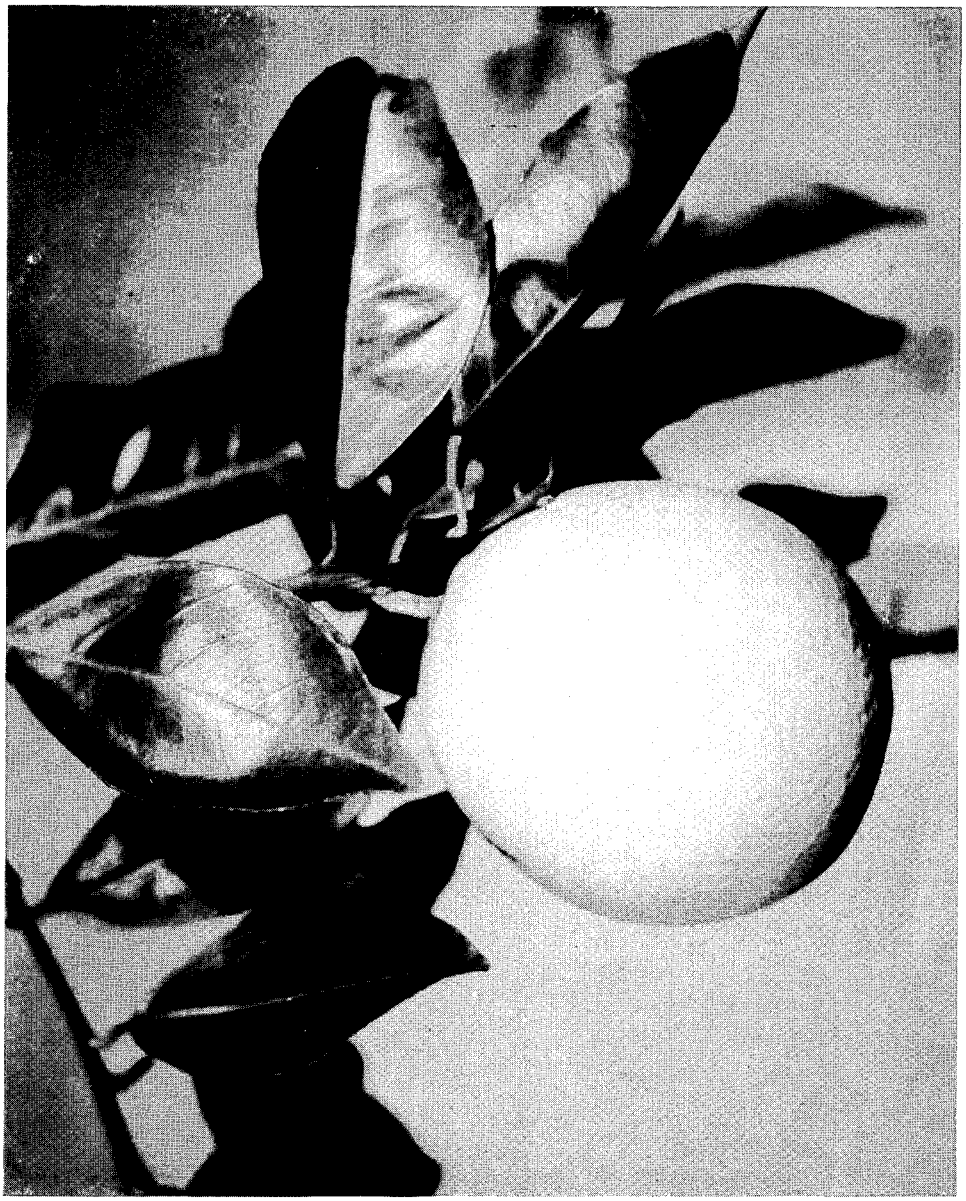
Figure 2:
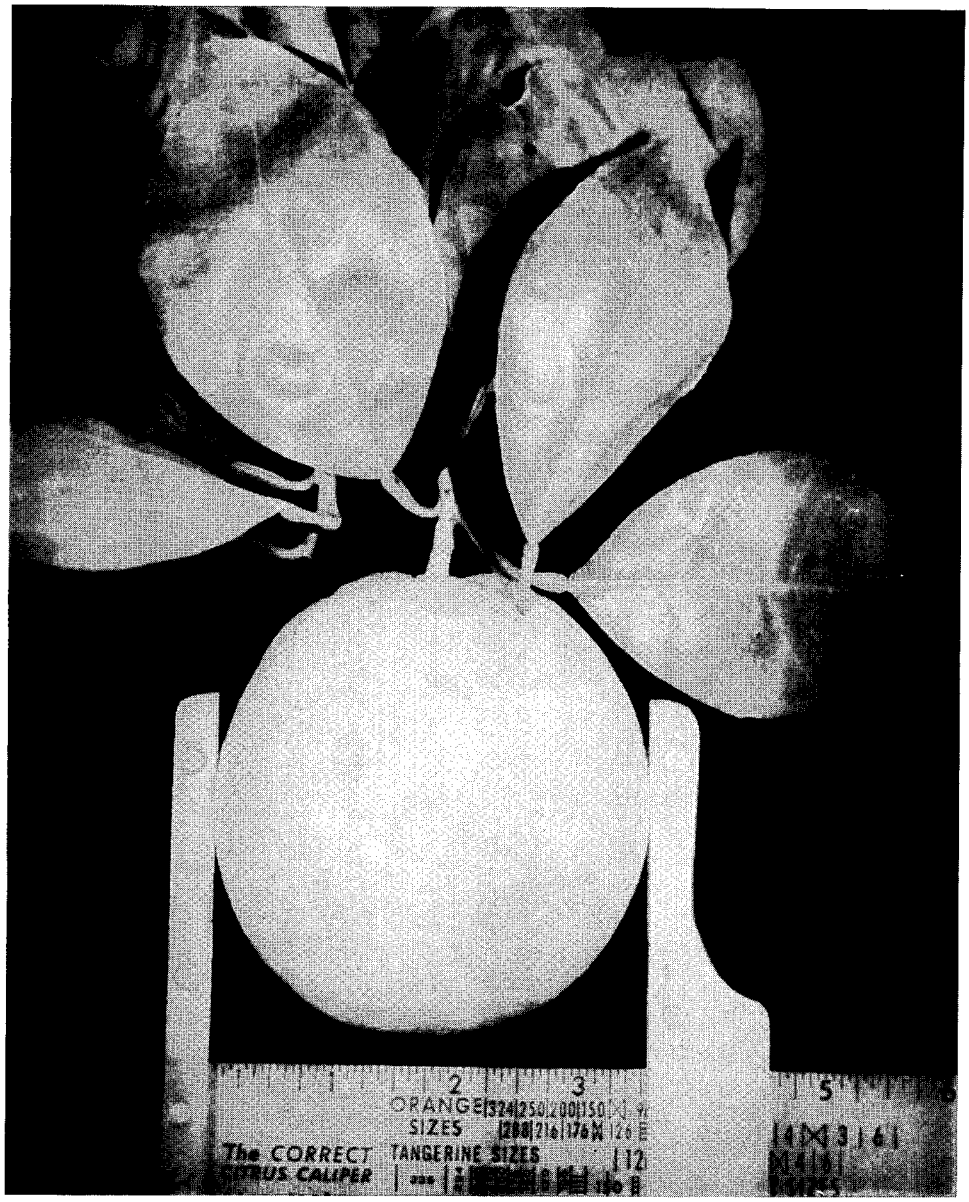

The accompanying illustration, Figure 1, shows a single fruit of my new variety, together with portions of the stem and leaves, while the illustration, Figure 2, is a view similar to Figure 1 including a measuring gauge applied to the fruit and indicating the transverse diameter thereof.

The following is a brief description in some detail of my new variety of orange with special relation to the leaves and fruit:

Tree: Upright with spreading branches, compact, vigorous and in general resembling the variety known as Parson Brown.

Leaves: Elliptical, large, deep glossy green above, somewhat lighter beneath.

Fruit:

*Form.*—Oblong globose or ovoid, slightly roughened at basal end.

*Size.*—Large, grading mostly 176 to 150 sizes, measuring $3\frac{1}{16}$ to $3\frac{5}{16}$ inches in transverse diameter; ratio of the diameters .95–.96.

*Rind.*—4.7 mm. thick, pebbly or roughened when fully matured, oil cells of medium size.

*Sections or locules.*—9 to 12, average 10.2 per fruit, separating readily.

*Juice content.*—Abundant, 5 gallons or more per standard Florida orange box.

*Flesh.*—Orange-yellow, coarse because of large juice sacs, quality unusually high for an early orange.

*Season.*—Early maturing, passing maturity tests as prescribed by Florida law in late September.

*Seeds.*—Present, average about 10 per fruit.

*Special features.*—Large size, abundant juice, early maturity when compared with other early oranges.

Below are given two charts showing the analytical results of comparative tests between the regular Parson Brown orange and my new variety orange. Both the tests and results were compiled by Dr. F. E. Gardner, Principal Horticulturalist, U. S. Department of Agriculture, Agricultural Research Administration, U. S. Subtropical Field Station, Orlando, Florida.

Chart No. 1, taken from oranges picked and tested September 17, 1952:

| | Regular Parson Brown | My New Variety |
|---|---|---|
| Av. diameter of fruit ... cm. | 6.2 | 7.0 |
| Av. rind thickness ... mm. | 3.6 | 3.1 |
| Av. No. of seeds | 15 | 14 |
| Percent Juice | 36 | 33 |
| Total soluble solids ... percent | 8.97 | 8.97 |
| Percent Acid | 1.53 | 1.37 |
| Solids/Acid ratio | 5.86 | 6.55 |

From the above chart, it will be noted that the soluble solids of both my new variety and the regular Parson Brown orange are identical and almost meet the minimum maturity requirements of 9.0% solids. However, due to the high acid content of both fruits, neither is yet ready for passing legal maturity tests. But from the .16% acid decrease in my new variety orange it appears the new variety is appreciably earlier in maturity than the regular Parson Brown.

Chart No. 2, taken from oranges picked and tested on October 9, 1952:

| | Regular Parson Brown | My New Variety |
|---|---|---|
| Av. diameter of fruit | 6.5 | 7.3 |
| Total soluble solids ... percent | 9.55 | 9.55 |
| Percent acid | 1.18 | 1.08 |
| Solids/Acid ratio | 8.09 | 8.84 |

As will be noted from this chart, the new variety orange continues to show a much larger fruit size, a better skin texture and a lower acid content than the regular Parson Brown orange, making it an earlier maturing orange than the regular Parson Brown.

Comparative tests have been conducted by the University of Florida, College of Agriculture, at Gainesville, Florida, on a large number of samples of my new variety of orange, Parson Brown oranges from my own orchard, and on Parson Brown oranges obtained from the University of Florida orchard. A summary of the test data comparing the oranges after all have passed maturity follows:

| | My New Variety | | Parson Brown (My Orchard) | Parson Brown (University of Florida orchard) | |
|---|---|---|---|---|---|
| Size | 150 | 176 | 216 | 150 | 176 |
| Diameter (in.) | 3 3/16 | 2 15/16 | 2 11/16 | 3 | 2 15/16 |
| Height | 3 5/16 | 3 1/16 | 2 11/16 | 2 15/16 | 2 13/16 |
| D/H | .966 | .95 | 1.006 | 1.02 | 1.03 |
| No. of sections | 10.2 | 9.6 | 10.0 | 10.2 | 10.8 |
| No. of seeds | 10.8 | 9.6 | 9.4 | 16.0 | 15.4 |
| Juice per fruit (ml.) | 129.7 | 96.8 | 91.7 | 116.6 | 99.0 |
| Rind thickness (mm.) | 4.70 | 4.08 | 4.74 | 4.3 | 3.54 |
| Gallons per box (juice) | 5.1 | 4.5 | 5.29 | 4.6 | 4.6 |
| Brix | 11.1 | 11.8 | 12.9 | 10.5 | 10.3 |
| Acid | .83 | .73 | .72 | 1.26 | 1.36 |
| Ratio (brix/acid) | 13.37 | 16.16 | 17.91 | 8.33 | 7.57 |

It will be noted from the above description that my variety of orange tree resembles the Parson Brown variety as regards the tree, heavy foliage, and size and shape of the leaves, although less thorny, but resembles the Florida navel as to the size and shape of the orange in that the present orange is slightly oblong and has more rag and coarser meat than the Parson Brown. My new variety of orange tree begins blooming in January and February, begins maturing in late September, and fully matures in early December, the maturity in the early stage being five to six weeks in advance of the Parson Brown. The flavor is very pleasant and easily distinguished from the Parson Brown orange. It is evident that the early maturity of my new variety of orange makes possible an earlier and larger shipping season for the citrus growers, whereas the large size of the orange, its abundant juice content and its rich flavor will be attractive and nutritionally beneficial to consumers.

Having thus disclosed my invention, what is claimed as new is:

A new and distinct variety of orange tree substantially as described and illustrated, characterized particularly by its earlier maturity, its larger fruit, its greater juice content per fruit, and the oblong globose shape of its fruit; all as compared with the Parson Brown orange.

BERTMAN V. JOHNSON.

No references cited.